(12) United States Patent
Miyoshi et al.

(10) Patent No.: US 8,476,260 B2
(45) Date of Patent: Jul. 2, 2013

(54) ANTITUMOR AGENT

(75) Inventors: Shinji Miyoshi, Osaka (JP); Shinsuke Ooike, Osaka (JP); Kazunori Iwata, Osaka (JP); Hidemasa Hikawa, Osaka (JP); Kunio Sugahara, Osaka (JP)

(73) Assignee: Mitsubishi Tanabe Pharma Corporation, Osaka-shi (JP)

( * ) Notice: Subject to any disclaimer, the term of this patent is extended or adjusted under 35 U.S.C. 154(b) by 275 days.

(21) Appl. No.: 12/810,564

(22) PCT Filed: Dec. 26, 2008

(86) PCT No.: PCT/JP2008/073864
§ 371 (c)(1),
(2), (4) Date: Jun. 25, 2010

(87) PCT Pub. No.: WO2009/084693
PCT Pub. Date: Jul. 9, 2009

(65) Prior Publication Data
US 2010/0286127 A1    Nov. 11, 2010

(30) Foreign Application Priority Data
Dec. 28, 2007 (JP) .................................. 2007-339456

(51) Int. Cl.
| | | |
|---|---|---|
| *A61P 35/00* | (2006.01) | |
| *A61P 43/00* | (2006.01) | |
| *A61K 31/55* | (2006.01) | |
| *A61K 45/00* | (2006.01) | |
| *C07D 495/14* | (2006.01) | |

(52) U.S. Cl.
USPC ........................................ 514/220; 540/560

(58) Field of Classification Search
USPC ........................................ 514/220; 540/560
See application file for complete search history.

(56) References Cited

U.S. PATENT DOCUMENTS

| | | | |
|---|---|---|---|
| 5,712,274 A | 1/1998 | Sueoka et al. | |
| 5,721,231 A | 2/1998 | Moriwaki et al. | |
| 7,015,213 B1 | 3/2006 | Bigg et al. | |

FOREIGN PATENT DOCUMENTS

| | | | |
|---|---|---|---|
| EP | 0 692 483 A1 | 1/1996 | |
| EP | 0 989 131 A1 | 3/2000 | |
| EP | 1 877 008 A1 | 2/2008 | |
| JP | 2008-156311 A | 7/2008 | |
| WO | WO 94/22872 A1 | 10/1994 | |
| WO | WO 98/11111 A1 | 3/1998 | |
| WO | WO 99/65917 A1 | 12/1999 | |
| WO | WO 2006/129623 A1 | 12/2006 | |

OTHER PUBLICATIONS

Filippakopoulos et al., *Nature*, 468(7327): 1067-1073 (2010).
French et al., *Oncogene*, 27(15): 2237-2242 (2008).
Ryan et al., *Current Opinion in Structural Biology*, 15(4): 441-446 (2005).
European Patent Office, Extended European Search Report in European Patent Application No. 08866818.1 (Dec. 9, 2011).
Dhalluin et al., *Nature*, 399: 491-496 (Jun. 3, 1999).
French et al., *American Journal of Pathology*, 159(6): 1987-1992 (Dec. 2001).
French et al., *Cancer Research*, 63: 304-307 (Jan. 15, 2003).
French et al., *Journal of Clinical Oncology*, 22(20): 4135-4139 (Oct. 15, 2004).
French et al., *Oncogene*, advance online publication, doi: 10.1038 / sj.onc.1210852 (Oct. 15, 2007).
Wu et al., *Journal of Biological Chemistry*, 282(18): 13141-13145 (May 4, 2007).
Yoshida et al., *Cancer Research*, 47: 3688-3691 (Jul. 15, 1987).
Yoshida et al., *Experimental Cell Research*, 177: 122-131 (1998).
Gunji et al., *Journal of Clinical Investigation*, 89(3): 954-960 (1992).
Minta et al., *American Journal of Pathology*, 119(1): 111-126 (1985).

*Primary Examiner* — Brenda Coleman
(74) *Attorney, Agent, or Firm* — Leydig, Voit & Mayer, Ltd.

(57) ABSTRACT

The present invention relates to a novel antitumor agent containing a compound that inhibits binding between acetylated histone and a bromodomain-containing protein, preferably a thienotriazolodiazepine compound represented by the following formula (I)

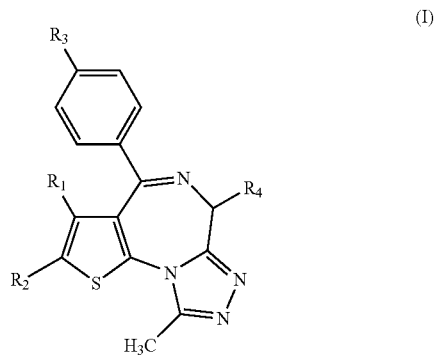

wherein each symbol is as defined in the description, or a pharmaceutically acceptable salt thereof or a hydrate or solvate as an active ingredient.

13 Claims, No Drawings

ANTITUMOR AGENT

TECHNICAL FIELD

The present invention relates to an antitumor agent comprising a compound that inhibits binding between acetylated histone and a bromodomain-containing protein as an active ingredient, more specifically an antitumor agent containing a thienotriazolodiazepine compound as an active ingredient.

BACKGROUND ART

Histone is a basic protein ion-bonded to genomic DNA, which is commonly present in the nucleus of eukaryotic cells of from multicellular organisms including human to unicellular organisms represented by fungus (mold, yeast). Histone generally consists of 5 kinds of components (H1, H2A, H2B, H3 and H4), which are highly similar beyond biological species. In the case of histone H4, for example, budding yeast histone H4 (full-length 102 amino acid sequence) and human histone H4 (full-length 102 amino acid sequence) are identical in 92% of the amino acid sequences and differ only in 8 residues. Among the natural proteins assumed to be present in several tens of thousand kinds in one organism, histone is known to be a protein most highly preserved among eucaryotic species. Genomic DNA is folded due to a regular bond to the histone, and a complex of the both forms a basic structural unit called nucleosome. Then, coagulation of the nucleosomes forms a chromosomal chromatin structure. Histone is subject to modification such as acetylation, methylation, phosphorylation, ubiquitination, sumolation and the like at an N-terminal portion called a histone tail, and maintains or specifically converts the chromatin structure to control reactions occurring on chromosomal DNA such as gene expression, DNA replication, DNA repair and the like. Post-translational modification of histone is an epigenetic regulatory mechanism, and is considered essential for the gene regulation of eukaryotic cells. For example, acetylation of histone is controlled by a pair of modification enzymes (i.e., histone acetylation enzyme and deacetylation enzyme). Generally, deacetylation enzymes act dominantly, and histone is maintained in a deacetylated state. When a cell is activated by stimulation, histone acetylation enzyme acetylates amino group of the lysine residue of histone and neutralizes the positive charge of the amino group. As a result, the interactions between nucleosomes become loose and transcription factor is recruited to start the transcription.

As a domain structure of proteins bound to acetylated lysine of histone, bromodomain is known. Humans have thirty-some kinds of bromodomain-containing proteins. Among them, BRD2, BRD3 and BRD4 are the proteins interacting with acetylated histone H3/H4. Among them, BRD4 is known to be a protein involved in the cell cycle and gene expression (non-patent document 1: Nature 399, 491-496, 1999) (non-patent document 2: JOURNAL OF BIOLOGICAL CHEMISTRY Vol. 282 No. 18 13141-13145, 2007). BRD4 belongs to a BET (bromodomain and extraterminal) family protein having two bromodomains and one extraterminal domain in a molecule. As the BET family proteins other than BRD4, BRD2, BRD3 and BRDt derived from human are known. Heretofore, a compound that inhibits binding between such BET family proteins and acetylated histone is not known.

In connection with the acetylation of histone, a compound inhibiting histone deacetylation enzyme is known to show cell cycle discontinuation, differentiation induction and apoptosis induction activity on tumor cells (non-patent document 3: Exp. Cell Res., 177, 122-131, 1988, non-patent document 4: Cancer Res., 47, 3688-3691, 1987). However, there is no report on whether or not a compound inhibiting binding between acetylated histone and a bromodomain-containing protein influences the tumor cells.

In recent years, there are some cases where BRD4-NUT fusion protein is expressed in epithelial cell carcinoma (midline carcinoma) in the upper tissue in the body such as thymus, airway, lung and the like. Patients showing expression of such fusion protein are known to resist radiation treatment and chemical therapy, and show poor prognosis (non-patent document 6: Cancer Research vol. 63 Jan. 15, 2003 p 304-307, non-patent document 7: Journal of clinical oncology Vol. 22 No. Oct. 15, 2004 p 4135-4139). In addition, it has been reported that, in midline carcinoma, t(9;15) chromosomal translocation of chromosome 9 and chromosome 15 also forms fusion protein BRD3-NUT of BRD3 protein and NUT protein. It has been reported that, in the cancer cell lines derived from patients expressing each of BRD3-NUT fusion protein and BRD4-NUT fusion protein, genetic inhibition of the expression of the fusion proteins by siRNA results in the discontinuation of the growth of the cancer cells (non-patent document 8: Oncogene advance online publication 15 Oct. 2007; doi: 10.1038/sj.onc.1210852). Hence, a medicament inhibiting the function of such fusion proteins is expected to be an antitumor agent. However, there is no report teaching that inhibition of binding between acetylated histone and bromodomain present on the fusion protein inhibits the functions of these fusion proteins.

On the other hand, it is known that a thienotriazolodiazepine compound represented by the following formula (I)

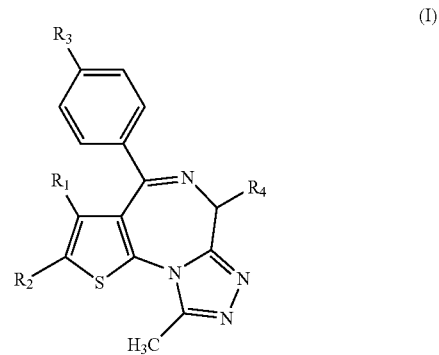

wherein
$R_1$ is alkyl having a carbon number of 1-4,
$R_2$ is a hydrogen atom; a halogen atom; or alkyl having a carbon number of 1-4 optionally substituted by a halogen atom or a hydroxyl group,
$R_3$ is a halogen atom; phenyl optionally substituted by a halogen atom, alkyl having a carbon number of 1-4, alkoxy having a carbon number of 1-4 or cyano; —$NR_5$—$(CH_2)_m$—$R_6$ wherein $R_5$ is a hydrogen atom or alkyl having a carbon number of 1-4, m is an integer of 0-4, and $R_6$ is phenyl or pyridyl optionally substituted by a halogen atom; or —$NR_7$—CO—$(CH_2)_n$—$R_8$ wherein $R_7$ is a hydrogen atom or alkyl having a carbon number of 1-4, n is an integer of 0-2, and $R_8$ is phenyl or pyridyl optionally substituted by a halogen atom, and
$R_4$ is —$(CH_2)_a$—CO—NH—$R_9$ wherein a is an integer of 1-4, and $R_9$ is alkyl having a carbon number of 1-4; hydroxyalkyl having a carbon number of 1-4; alkoxy having a carbon number of 1-4; or phenyl or pyridyl optionally substituted by alkyl having a carbon number of 1-4, alkoxy having a carbon number of 1-4, amino or a hydroxyl group or —$(CH_2)_b$—$COOR_{10}$ wherein b is an integer of 1-4, and $R_{10}$ is alkyl having a carbon number of 1-4, has a cell adhesion inhibitory action and is useful for inflammatory intestine diseases, and has an action inhibiting costimulatory signals from CD28 on T cells and is useful for the rejection during transplantation, autoimmune diseases and allergic diseases (patent document 1: WO 98/11111, patent document 2: WO 2006/129623). However, it is not known at all that these compounds have an action to inhibit binding between acetylated histone and BET family protein, and an antitumor action.

patent document 1: WO 98/11111
patent document 2: WO 2006/129623
non-patent document 1: Nature 399, p 491-496, 1999
non-patent document 2: JOURNAL OF BIOLOGICAL CHEMISTRY Vol. 282 No. 18 p 13141-13145, 2007
non-patent document 3: Exp. Cell Res., 177, p 122-131, 1988
non-patent document 4: Cancer Res., 47, p 3688-3691, 1987
non-patent document 5: American Journal of Pathology Vol. 159 No. 6, p 1987-1992 December 2001
non-patent document 6: Cancer Research vol. 63, p 304-307 Jan. 15, 2003
non-patent document 7: Journal of clinical oncology Vol. 22 No. 20, p 4135-4139 Oct. 15, 2004
non-patent document 8: Oncogene advance online publication 15 Oct. 2007; doi: 10.1038/sj.onc.1210852

DISCLOSURE OF THE INVENTION

Problems to be Solved by the Invention

An object of the present invention is to provide a novel antitumor agent.

Means of Solving the Problems

The present inventors have conducted intensive studies in an attempt to solve the aforementioned problems and found that a novel antitumor agent can be provided by using a compound that inhibits binding between acetylated histone and a bromodomain-containing protein, preferably a thienotriazolodiazepine compound represented by the following formula (I) or a pharmaceutically acceptable salt thereof or a hydrate or solvate thereof as an active ingredient, which resulted in the completion of the present invention.

Accordingly, the gist of the present invention is as follows.
1. An antitumor agent comprising a compound that inhibits binding between acetylated histone and a bromodomain-containing protein or a pharmaceutically acceptable salt thereof or a hydrate or solvate thereof as an active ingredient,
2. the antitumor agent of 1, wherein the acetylated histone is acetylated histone H3 or acetylated histone H4,
3. the antitumor agent of claim 1 or 2, wherein the acetylated histone is acetylated histone H4,
4. the antitumor agent of any one of 1 to 3, wherein the bromodomain-containing protein is a BET family protein,
5. the antitumor agent of 4, wherein the BET family protein is BRD2, BRD3, BRD4 or BRDt,
6. the antitumor agent of claim 4 or 5, wherein the BET family protein is BRD2, BRD3 or BRD4,
7. the antitumor agent of any one of 1 to 6, wherein the compound that inhibits binding between acetylated histone and a bromodomain-containing protein is a thienotriazolodiazepine compound represented by the following formula (I)

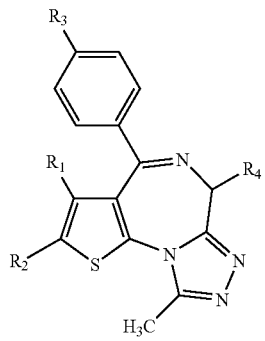

wherein
$R_1$ is alkyl having a carbon number of 1-4,
$R_2$ is a hydrogen atom; a halogen atom; or alkyl having a carbon number of 1-4 optionally substituted by a halogen atom or a hydroxyl group,
$R_3$ is a halogen atom; phenyl optionally substituted by a halogen atom, alkyl having a carbon number of 1-4, alkoxy having a carbon number of 1-4 or cyano; —$NR_5$—$(CH_2)_m$—$R_6$ wherein $R_5$ is a hydrogen atom or alkyl having a carbon number of 1-4, m is an integer of 0-4, and $R_6$ is phenyl or pyridyl optionally substituted by a halogen atom; or —$NR_7$—CO—$(CH_2)_n$—$R_8$ wherein $R_7$ is a hydrogen atom or alkyl having a carbon number of 1-4, n is an integer of 0-2, and $R_8$ is phenyl or pyridyl optionally substituted by a halogen atom, and
$R_4$ is —$(CH_2)_a$—CO—NH—$R_9$ wherein a is an integer of 1-4, and $R_9$ is alkyl having a carbon number of 1-4; hydroxyalkyl having a carbon number of 1-4; alkoxy having a carbon number of 1-4; or phenyl or pyridyl optionally substituted by alkyl having a carbon number of 1-4, alkoxy having a carbon number of 1-4, amino or a hydroxyl group or —$(CH_2)_b$—$COOR_{10}$ wherein b is an integer of 1-4, and $R_{10}$ is alkyl having a carbon number of 1-4,
or a pharmaceutically acceptable salt thereof or a hydrate or solvate thereof,
8. the antitumor agent of 7, wherein the steric configuration of an asymmetric carbon atom to which substituent $R_4$ in the formula (I) is bonded is an S configuration,
9. the antitumor agent of claim 7 or 8, wherein $R_1$ in the formula (I) is methyl,
10. the antitumor agent of any one of 7 to 9, wherein $R_2$ in the formula (I) is methyl,
11. the antitumor agent of any one of 7 to 10, wherein $R_3$ in the formula (I) is a chlorine atom, cyanophenyl, phenylamino or phenethylcarbonylamino,
12. the antitumor agent of any one of 7 to 11, wherein $R_4$ in the formula (I) is hydroxyphenylaminocarbonylmethyl or methoxycarbonylmethyl,
13. the antitumor agent of any one of 7 to 12, wherein the compound represented by the formula (I) is (S)-2-[4-(4-chlorophenyl)-2,3,9-trimethyl-6H-thieno[3,2-f][1,2,4]triazolo[4,3-a][1,4]diazepin-6-yl]-N-(4-hydroxyphenyl)acetamide or a dihydrate thereof,
methyl (S)-{4-(3'-cyanobiphenyl-4-yl)-2,3,9-trimethyl-6H-thieno[3,2-f][1,2,4]triazolo[4,3-a][1,4]diazepin-6-yl}acetate,
methyl (S)-{2,3,9-trimethyl-4-(4-phenylaminophenyl)-6H-thieno[3,2-f][1,2,4]triazolo[4,3-a][1,4]diazepin-6-yl}acetate or methyl (S)-{2,3,9-trimethyl-4-[4-(3-phenylpropionylamino)phenyl]-6H-thieno[3,2-f][1,2,4]triazolo[4,3-a][1,4]diazepin-6-yl}acetate, 14. the antitumor agent of any one of 1 to 13, wherein the cancer is hematologic cancer, myeloma, liver cancer, ovarian cancer, prostate cancer, lung cancer, osteosarcoma or colorectal cancer, 15. an anti-lung cancer agent comprising (S)-2-[4-(4-chlorophenyl)-2,3,9-trimethyl-6H-thieno[3,2-f][1,2,4]triazolo[4,3-a][1,4]diazepin-6-yl]-N-(4-hydroxyphenyl)acetamide or a dihydrate thereof as an active ingredient, 16. an antitumor agent comprising, as an active ingredient, a thienotriazolodiazepine compound represented by the following formula (I)

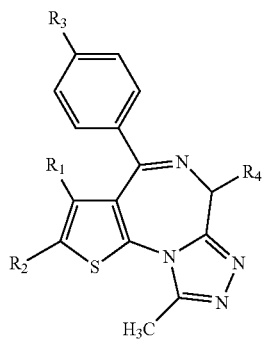

(I)

wherein $R_1$ is alkyl having a carbon number of 1-4, $R_2$ is a hydrogen atom; a halogen atom; or alkyl having a carbon number of 1-4 optionally substituted by a halogen atom or a hydroxyl group, $R_3$ is a halogen atom; phenyl optionally substituted by a halogen atom, alkyl having a carbon number of 1-4, alkoxy having a carbon number of 1-4 or cyano; —$NR_5$—$(CH_2)_m$—$R_6$ wherein $R_5$ is a hydrogen atom or alkyl having a carbon number of 1-4, m is an integer of 0-4, and $R_6$ is phenyl or pyridyl optionally substituted by a halogen atom; or —$NR_7$—CO—$(CH_2)_n$—$R_8$ wherein $R_7$ is a hydrogen atom or alkyl having a carbon number of 1-4, n is an integer of 0-2, and $R_8$ is phenyl or pyridyl optionally substituted by a halogen atom, and $R_4$ is —$(CH_2)_a$—CO—NH—$R_9$ wherein a is an integer of 1-4, and $R_9$ is alkyl having a carbon number of 1-4; hydroxyalkyl having a carbon number of 1-4; alkoxy having a carbon number of 1-4; or phenyl or pyridyl optionally substituted by alkyl having a carbon number of 1-4, alkoxy having a carbon number of 1-4, amino or a hydroxyl group or —$(CH_2)_b$—$COOR_{10}$ wherein b is an integer of 1-4, and $R_{10}$ is alkyl having a carbon number of 1-4, or a pharmaceutically acceptable salt thereof or a hydrate or solvate thereof, 17. an inhibitor of binding between acetylated histone and a bromodomain-containing protein, comprising, as an active ingredient, a thienotriazolodiazepine compound represented by the following formula (I)

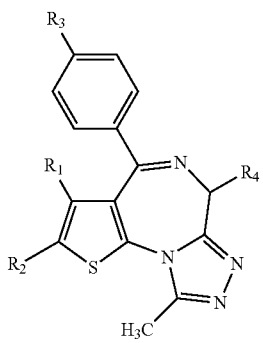

(I)

wherein $R_1$ is alkyl having a carbon number of 1-4, $R_2$ is a hydrogen atom; a halogen atom; or alkyl having a carbon number of 1-4 optionally substituted by a halogen atom or a hydroxyl group, $R_3$ is a halogen atom; phenyl optionally substituted by a halogen atom, alkyl having a carbon number of 1-4, alkoxy having a carbon number of 1-4 or cyano; —$NR_5$—$(CH_2)_m$—$R_6$ wherein $R_5$ is a hydrogen atom or alkyl having a carbon number of 1-4, m is an integer of 0-4, and $R_6$ is phenyl or pyridyl optionally substituted by a halogen atom; or —$NR_7$—CO—$(CH_2)_n$—$R_8$ wherein $R_7$ is a hydrogen atom or alkyl having a carbon number of 1-4, n is an integer of 0-2, and $R_8$ is phenyl or pyridyl optionally substituted by a halogen atom, and $R_4$ is —$(CH_2)_a$—CO—NH—$R_9$ wherein a is an integer of 1-4, and $R_9$ is alkyl having a carbon number of 1-4; hydroxyalkyl having a carbon number of 1-4; alkoxy having a carbon number of 1-4; or phenyl or pyridyl optionally substituted by alkyl having a carbon number of 1-4, alkoxy having a carbon number of 1-4, amino or a hydroxyl group or —$(CH_2)_b$—$COOR_{10}$ wherein b is an integer of 1-4, and $R_{10}$ is alkyl having a carbon number of 1-4, or a pharmaceutically acceptable salt thereof or a hydrate or solvate thereof, 18. a method of treating cancer, comprising administering an effective amount of a compound that inhibits binding between acetylated histone and a bromodomain-containing protein or a pharmaceutically acceptable salt thereof or a hydrate or solvate thereof to a mammal, 19. a method of treating cancer, comprising administering an effective amount of a thienotriazolodiazepine compound which inhibits binding between acetylated histone and a bromodomain-containing protein and is represented by the following formula (I)

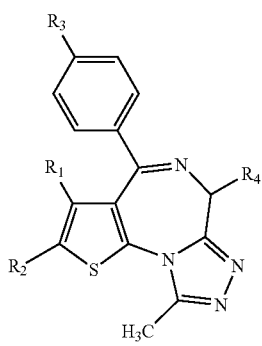

wherein

R₁ is alkyl having a carbon number of 1-4,

R₂ is a hydrogen atom; a halogen atom; or alkyl having a carbon number of 1-4 optionally substituted by a halogen atom or a hydroxyl group, R₃ is a halogen atom; phenyl optionally substituted by a halogen atom, alkyl having a carbon number of 1-4, alkoxy having a carbon number of 1-4 or cyano; —NR₅—(CH₂)$_m$—R₆ wherein R₅ is a hydrogen atom or alkyl having a carbon number of 1-4, m is an integer of 0-4, and R₆ is phenyl or pyridyl optionally substituted by a halogen atom; or —NR₇—CO—(CH₂)$_n$—R₈ wherein R₇ is a hydrogen atom or alkyl having a carbon number of 1-4, n is an integer of 0-2, and R₈ is phenyl or pyridyl optionally substituted by a halogen atom, and R₄ is —(CH₂)$_a$—CO—NH—R₉ wherein a is an integer of 1-4, and R₉ is alkyl having a carbon number of 1-4; hydroxyalkyl having a carbon number of 1-4; alkoxy having a carbon number of 1-4; or phenyl or pyridyl optionally substituted by alkyl having a carbon number of 1-4, alkoxy having a carbon number of 1-4, amino or a hydroxyl group) or —(CH₂)$_b$—COOR₁₀ wherein b is an integer of 1-4, and R₁₀ is alkyl having a carbon number of 1-4, or a pharmaceutically acceptable salt thereof or a hydrate or solvate thereof to a mammal, 20. use of a compound that inhibits binding between acetylated histone and a bromodomain-containing protein or a pharmaceutically acceptable salt thereof or a hydrate or solvate thereof for the production of an agent for the prophylaxis or treatment of cancer, 21. use of a thienotriazolodiazepine compound which inhibits binding between acetylated histone and a bromodomain-containing protein and is represented by the following formula (I)

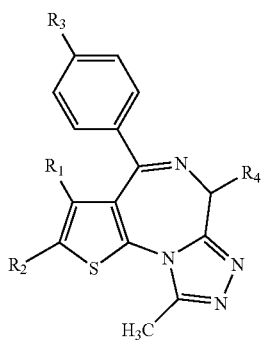

wherein

R₁ is alkyl having a carbon number of 1-4,

R₂ is a hydrogen atom; a halogen atom; or alkyl having a carbon number of 1-4 optionally substituted by a halogen atom or a hydroxyl group, R₃ is a halogen atom; phenyl optionally substituted by a halogen atom, alkyl having a carbon number of 1-4, alkoxy having a carbon number of 1-4 or cyano; —NR₅—(CH₂)$_m$—R₆ wherein R₅ is a hydrogen atom or alkyl having a carbon number of 1-4, m is an integer of 0-4, and R₆ is phenyl or pyridyl optionally substituted by a halogen atom; or —NR₇—CO—(CH₂)$_n$—R₈ wherein R₇ is a hydrogen atom or alkyl having a carbon number of 1-4, n is an integer of 0-2, and R₈ is phenyl or pyridyl optionally substituted by a halogen atom, and R₄ is —(CH₂)$_a$—CO—NH—R₉ wherein a is an integer of 1-4, and R₉ is alkyl having a carbon number of 1-4; hydroxyalkyl having a carbon number of 1-4; alkoxy having a carbon number of 1-4; or phenyl or pyridyl optionally substituted by alkyl having a carbon number of 1-4, alkoxy having a carbon number of 1-4, amino or a hydroxyl group or —(CH₂)$_b$—COOR₁₀ wherein b is an integer of 1-4, and R₁₀ is alkyl having a carbon number of 1-4, or a pharmaceutically acceptable salt thereof or a hydrate or solvate thereof for the production of an agent for the prophylaxis or treatment of cancer, 22. a compound that inhibits binding between acetylated histone and a bromodomain-containing protein or a pharmaceutically acceptable salt thereof or a hydrate or solvate thereof, to be used for a method for the prophylaxis or treatment of cancer, 23. a thienotriazolodiazepine compound which inhibits binding between acetylated histone and a bromodomain-containing protein and is represented by the following formula (I)

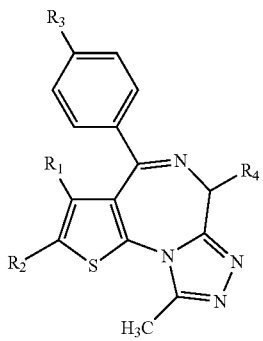

wherein

R₁ is alkyl having a carbon number of 1-4,

R₂ is a hydrogen atom; a halogen atom; or alkyl having a carbon number of 1-4 optionally substituted by a halogen atom or a hydroxyl group, R₃ is a halogen atom; phenyl optionally substituted by a halogen atom, alkyl having a carbon number of 1-4, alkoxy having a carbon number of 1-4 or cyano; —NR₅—(CH₂)$_m$—R₆ wherein R₅ is a hydrogen atom or alkyl having a carbon number of 1-4, m is an integer of 0-4, and R₆ is phenyl or pyridyl optionally substituted by a halogen atom; or —NR₇—CO—(CH₂)$_n$—R₈ wherein R₇ is a hydrogen atom or alkyl having a carbon number of 1-4, n is an integer of 0-2, and R₈ is phenyl or pyridyl optionally substituted by a halogen atom, and R₄ is —(CH₂)$_a$—CO—NH—R₉ wherein a is an integer of 1-4, and R₉ is alkyl having a carbon number of 1-4; hydroxyalkyl having a carbon number of 1-4; alkoxy having a carbon number of 1-4; or phenyl or pyridyl optionally substituted by alkyl having a carbon number of 1-4, alkoxy having a carbon number of 1-4, amino or a hydroxyl group or —(CH$_2$)$_b$—COOR$_{10}$ wherein b is an integer of 1-4, and R$_{10}$ is alkyl having a carbon number of 1-4, or a pharmaceutically acceptable salt thereof or a hydrate or solvate thereof, to be used for a method for the prophylaxis or treatment of cancer.

Effect of the Invention

The present invention can provide a novel antitumor agent.

BEST MODE FOR CARRYING OUT THE INVENTION

The antitumor agent provided by the present invention contains, as an active ingredient, a compound that inhibits binding between acetylated histone and a bromodomain-containing protein. As mentioned earlier, histone consists of 5 kinds of components and, in the present invention, a compound that inhibits binding between acetylated histone H3 or acetylated histone H4, wherein H3 or H4 is acetylated, and a bromodomain-containing protein is preferably used as an active ingredient. The bromodomain-containing protein is preferably a protein belonging to the BET family. The BET family protein is known to include, besides those derived from human, proteins derived from fly, yeast and the like. In the present invention, a compound that inhibits binding between a BET family protein derived from human and acetylated histone is preferably used as the active ingredient. Specific examples of the BET family protein derived from human include BRD2, BRD3, BRD4 and BRDt, with preference given to BRD2, BRD3 and BRD4. Therefore, a compound preferably used as an active ingredient in the present invention is a compound that inhibits binding between acetylated histone H3 or acetylated histone H4 (preferably, acetylated histone H4) and BRD2, BRD3 or BRD4.

Examples of the specific structure of the compound to be used as an active ingredient in the present invention include a thienotriazolodiazepine compound represented by the following formula (I)

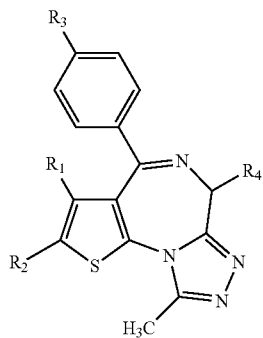

(I)

wherein

R$_1$ is alkyl having a carbon number of 1-4,

R$_2$ is a hydrogen atom; a halogen atom; or alkyl having a carbon number of 1-4 optionally substituted by a halogen atom or a hydroxyl group, R$_3$ is a halogen atom; phenyl optionally substituted by a halogen atom, alkyl having a carbon number of 1-4, alkoxy having a carbon number of 1-4 or cyano; —NR$_5$—(CH$_2$)$_m$—R$_6$ wherein R$_5$ is a hydrogen atom or alkyl having a carbon number of 1-4, m is an integer of 0-4, and R$_6$ is phenyl or pyridyl optionally substituted by a halogen atom; or —NR$_7$—CO—(CH$_2$)$_n$—R$_8$ wherein R$_7$ is a hydrogen atom or alkyl having a carbon number of 1-4, n is an integer of 0-2, and R$_8$ is phenyl or pyridyl optionally substituted by a halogen atom, and R$_4$ is —(CH$_2$)$_a$—CO—NH—R$_9$ wherein a is an integer of 1-4, and R$_9$ is alkyl having a carbon number of 1-4; hydroxyalkyl having a carbon number of 1-4; alkoxy having a carbon number of 1-4; or phenyl or pyridyl optionally substituted by alkyl having a carbon number of 1-4, alkoxy having a carbon number of 1-4, amino or a hydroxyl group or —(CH$_2$)$_b$—COOR$_{10}$ wherein b is an integer of 1-4, and R$_{10}$ is alkyl having a carbon number of 1-4, a pharmaceutically acceptable salt thereof and a hydrate or solvate thereof.

In the present specification, alkyl having a carbon number of 1-4 means straight chain or branched chain alkyl and, for example, methyl, ethyl, n-propyl, isopropyl, n-butyl, isobutyl, t-butyl and the like can be mentioned.

The halogen atom means a fluorine atom, a chlorine atom, a bromine atom or an iodine atom.

Alkoxy having a carbon number of 1-4 means straight chain or branched chain alkoxy and, for example, methoxy, ethoxy, n-propoxy, isopropoxy, n-butoxy, isobutoxy, t-butoxy and the like can be mentioned.

Hydroxyalkyl having a carbon number of 1-4 means the aforementioned alkyl having a carbon number of 1-4 and substituted by 1 to 9 hydroxy groups, and specific examples include hydroxymethyl, hydroxyethyl and the like.

A preferable example of R$_1$ is methyl.

Preferable examples of R$_2$ include a halogen atom, methyl and hydroxymethyl, more preferable examples include a chlorine atom, methyl and hydroxymethyl, and most preferable examples include methyl.

Preferable examples of R$_3$ include a halogen atom, methoxyphenyl, cyanophenyl, —NR$_{5'}$—(CH$_2$)$_{m'}$—R$_{6'}$ wherein R$_{5'}$ is a hydrogen atom or methyl, m' is 0 or 1, and R$_{6'}$ is phenyl, pyridyl or phenyl substituted by a fluorine atom and —NR$_{7'}$—CO—(CH$_2$)$_{n'}$—R$_{8'}$ wherein R$_{7'}$ is a hydrogen atom, n' is 2, and R$_{8'}$ is phenyl, and more preferable examples include a chlorine atom, cyanophenyl, phenylamino and phenethylcarbonylamino. Most preferable examples include a chlorine atom and 3-cyanophenyl.

Preferable examples of R$_4$ include —(CH$_2$)$_{a'}$—CO—NH—R$_{9'}$ wherein a' is 1, and R$_{9'}$ is methyl, hydroxyethyl, methoxy, aminophenyl, hydroxyphenyl, pyridyl or methoxypyridyl and —(CH$_2$)$_{b'}$—COOR$_{10'}$ wherein b' is 1, and R$_{10'}$ is methyl or ethyl, more preferable examples include hydroxyphenylaminocarbonylmethyl and methoxycarbonylmethyl. Most preferable examples include 4-hydroxyphenylaminocarbonylmethyl and methoxycarbonylmethyl. In addition, the carbon atom to which R$_4$ is bonded is an asymmetric carbon atom. The steric configuration thereof may be any of S configuration, R configuration and a mixture thereof, and S configuration is desirable.

Preferable examples of the compound represented by the formula (I) include (S)-2-[4-(4-chlorophenyl)-2,3,9-trimethyl-6H-thieno[3,2-f][1,2,4]triazolo[4,3-a][1,4]diazepin-6-yl]-N-(4-hydroxyphenyl)acetamide and a dihydrate thereof (compound 1 in Examples), methyl (S)-{4-(3'-cyanobiphenyl-4-yl)-2,3,9-trimethyl-6H-thieno[3,2-f][1,2,4]triazolo[4,3-a][1,4]diazepin-6-yl}acetate (compound 2 in Examples), methyl (S)-{2,3,9-trimethyl-4-(4-phenylaminophenyl)-6H-thieno[3,2-f][1,2,4]triazolo[4,3-a][1,4]diazepin-6-yl}acetate (compound 8 in Examples), and methyl (S)-{2,3,9-trimethyl-4-[4-(3-phenylpropionylamino)phenyl]-6H-thieno[3,2-f][1,2,4]triazolo[4,3-a][1,4]diazepin-6-yl}acetate (compound 10 in Examples), and more preferable examples include (S)-2-[4-(4-chlorophenyl)-2,3,9-trimethyl-6H-thieno[3,2-f][1,2,4]triazolo[4,3-a][1,4]diazepin-6-yl]-N-(4-hydroxyphenyl)acetamide and a dihydrate thereof.

The compound that can be used as an active ingredient in the present invention may be a compound in a free form or a pharmaceutically acceptable salt. Examples of the pharmaceutically acceptable salt include salts with mineral acids such as hydrochloric acid, sulfuric acid, hydrogen bromide salt, phosphoric acid and the like; salts with organic acids such as methanesulfonic acid, p-toluenesulfonic acid, acetic acid, oxalic acid, citric acid, malic acid, fumaric acid and the like; salts with alkali metals such as sodium, potassium and the like; salts with alkaline earth metals such as magnesium and the like; salts with amines such as ammonia, ethanolamine, 2-amino-2-methyl-1-propanol and the like. Besides these, the kind of the salt is not particularly limited as long as it is acceptable as a medicament.

Furthermore, the compound that can be used as an active ingredient in the present invention may be used as a solvate. Examples of the solvate include solvates with ethanol, ethyl acetate and the like. Besides this, the kind of the solvate is not particularly limited as long as it is acceptable as a medicament.

All the compounds represented by the formula (I) are known compounds, and can be easily synthesized by those of ordinary skill in the art according to the methods described in WO 98/11111, WO 2006/129623 and the like.

The active ingredient of the present invention can be mixed with a pharmaceutically acceptable carrier (excipient, binder, disintegrant etc.) and orally or parenterally administered in the form of a pharmaceutical composition or preparation (e.g., tablet, liquid etc.). A pharmaceutical composition can be prepared according to a conventional method.

The dose of the active ingredient is determined depending on the age, body weight, general health condition, sex, diet, administration time, administration method, clearance rate, drug combination and the disease state for which patients are under treatment at that time, and in consideration thereof or other factors. In a specific example, while the daily dose varies depending on the condition and body weight of patients, the kind of compound, administration route and the like, it is, for example, 0.01-1000 mg/kg body weight/day by oral administration, which is given in one to several portions a day, and it is about 0.01-100 mg/kg body weight/day by parenteral administration, which is given in one to several portions a day.

While the antitumor agent provided by the present invention can be applied to any cancer irrespective of its type, specific examples include hematologic cancer, myeloma, liver cancer, ovarian cancer, prostate cancer, lung cancer, osteosarcoma, colorectal cancer, breast cancer, skin cancer and epithelial cell cancer (midline carcinoma). Among those, suitable cancer type includes hematologic cancer, myeloma, liver cancer, ovarian cancer, prostate cancer, lung cancer, osteosarcoma and colorectal cancer, and more suitable cancer type includes hematologic cancer, prostate cancer, lung cancer and colorectal cancer. In the present invention, hematologic cancer includes lymphoma and leukemia. In the present invention, the antitumor agent is a concept including a carcinostatic agent, an antitumor medicine and the like, which is used for the prophylaxis and/or treatment of cancer and affords an effect of shrinking or killing cancer or preventing the growth of cancer. Moreover, in the present invention, the "prophylaxis" is an act of administration of the active ingredient of the present invention to a healthy subject who has not developed the disease, which aims, for example, to prevent onset of the disease. The "treatment" is an act of administration of the active ingredient of the present invention to a person diagnosed by a doctor to have developed the disease (patient), which aims, for example, to alleviate the disease or symptom, prevent the growth of carcinoma, or restore the state before onset of the disease. Even when the administration aims to prevent aggravation of the disease or symptom, or prevent the growth of carcinoma, it is an act of treatment when the subject of administration is a patient.

EXAMPLES

The present invention is explained in more detail in the following by referring Examples, which are not to be construed as limitative.

Synthetic Example

Compound 1 shown below was synthesized according to the method described in Example 2 of WO98/11111, and compound 2 was synthesized according, to the method described in Example 8 of WO2006/129623. Other compounds 3-18 were also synthesized in the same manner according to the methods described in the Examples of WO98/11111 or WO2006/129623.

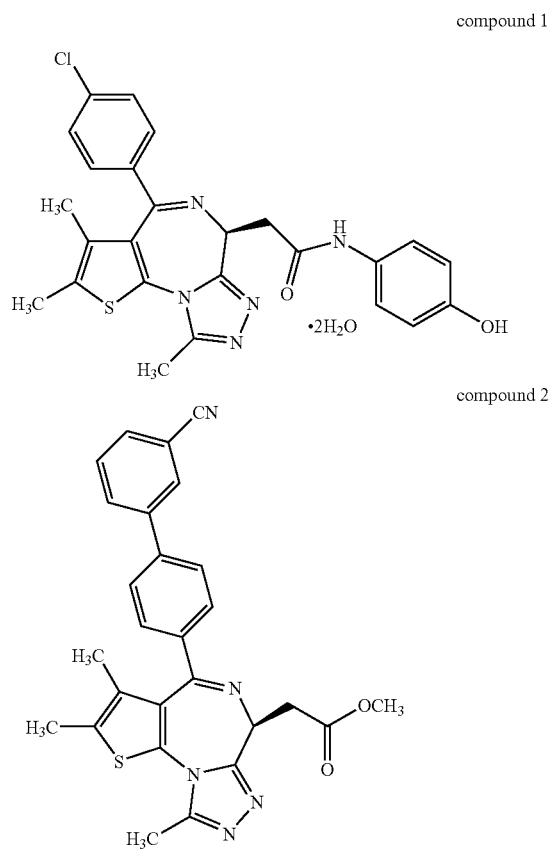

compound 3
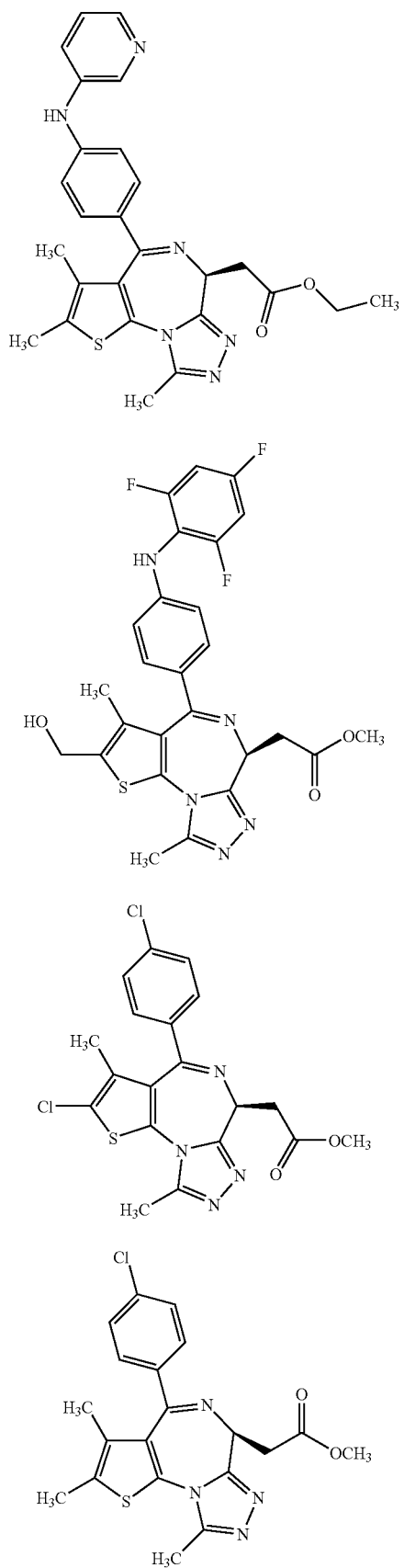
compound 4
compound 5
compound 6
compound 7
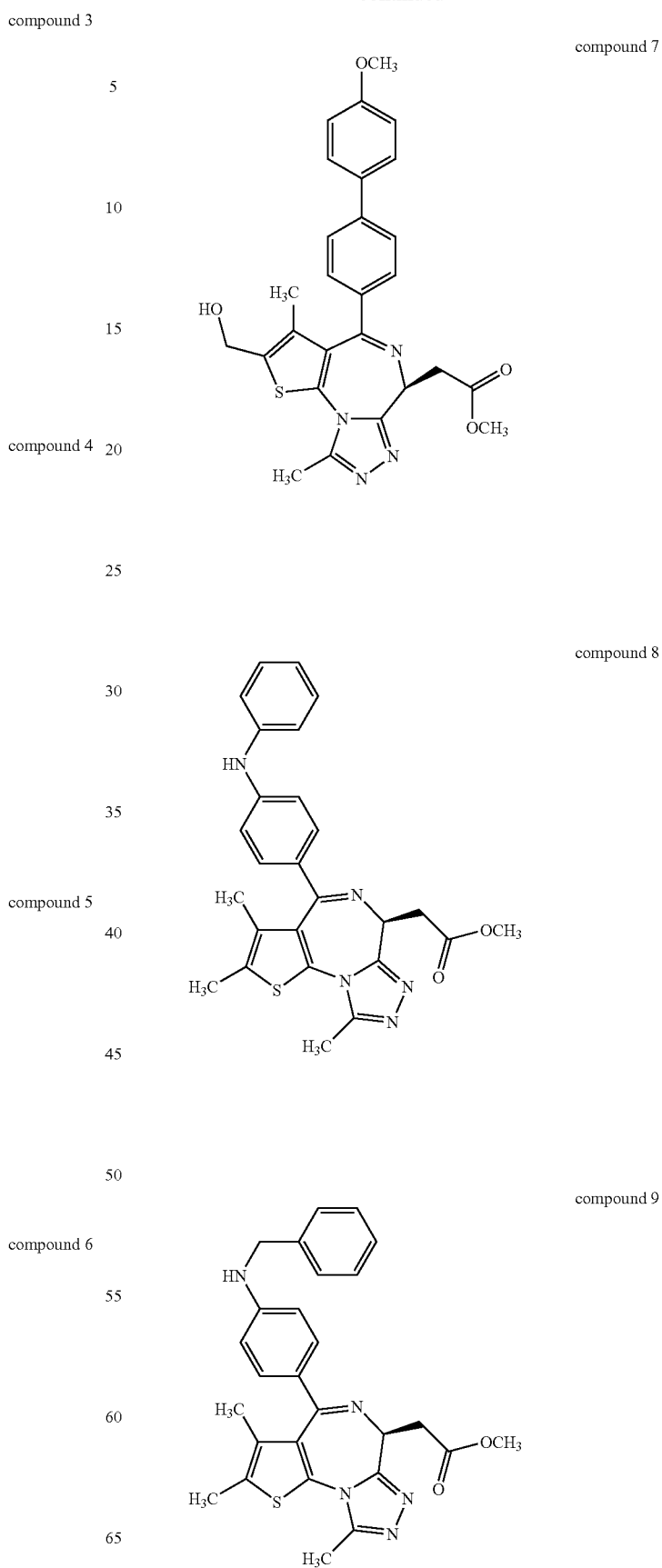
compound 8
compound 9

-continued
compound 10
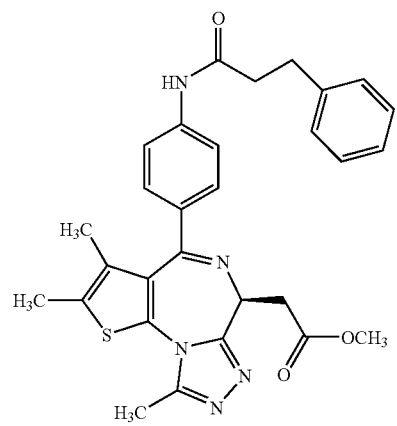
compound 11
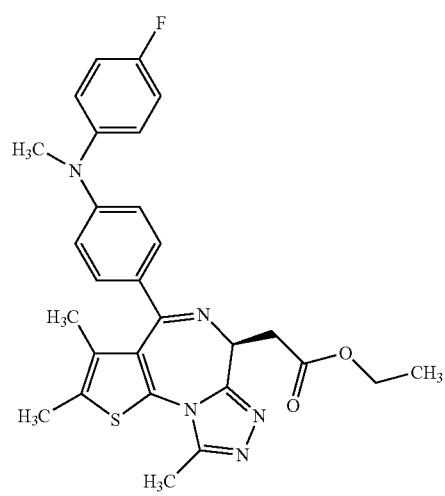
compound 12
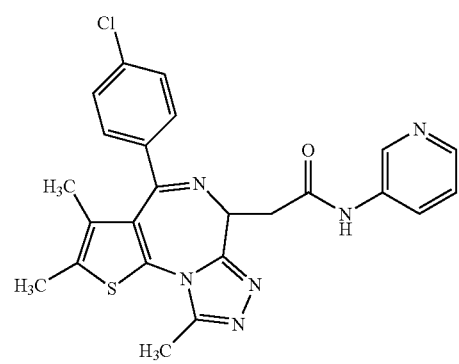
compound 13
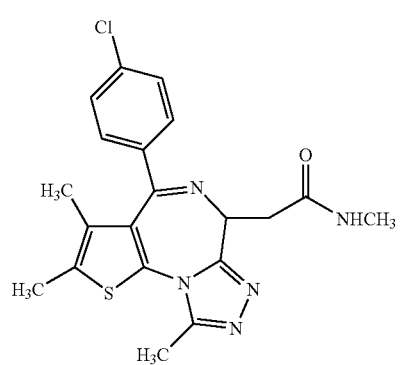
-continued
compound 14
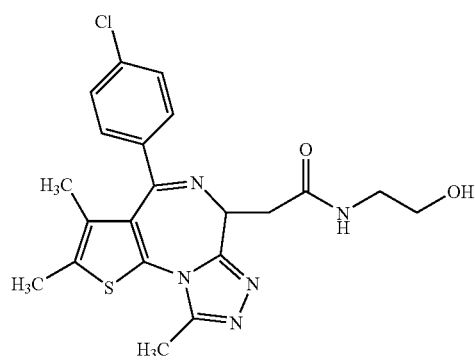
compound 15
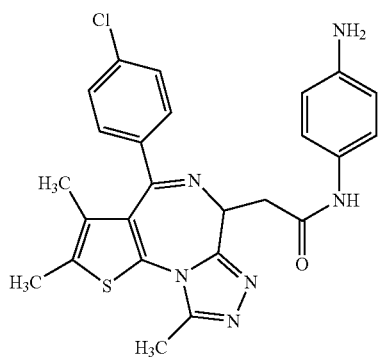
compound 16
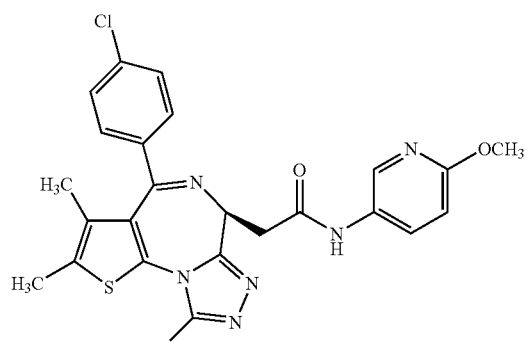
compound 17
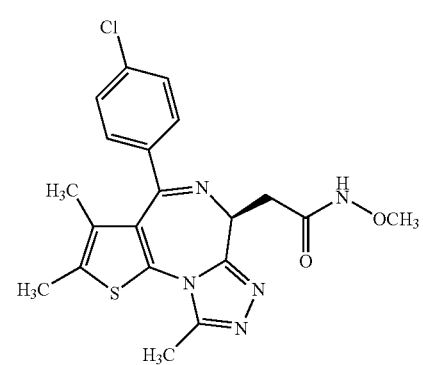

-continued compound 18

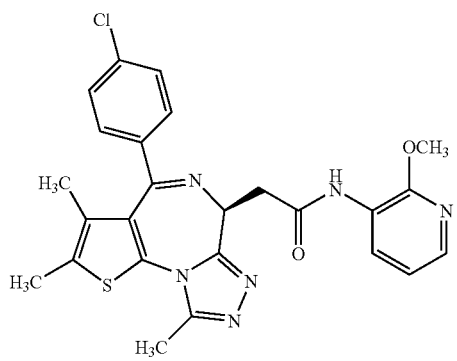

Example 1

Binding Inhibitory Test of Acetylated Histone H4 and BRD2, 3 and 4

An expression vector containing cDNA of BRD2, 3 and 4 added with Flag-tag was transfected to CHO cell, and a cell lysate was prepared 24 hr later. Binding of acetylated histone H4 and BRD was confirmed by a Time Resolved Fluorescence Resonance Energy Transfer (TR-FRET) method. To a 384-well white plate (manufactured by Coaster) were added 50 nmol/L biotin-labeled acetylated histone H4 peptide (manufactured by Upstate) and a serially diluted test compound. Furthermore, CHO cell lysate transfected with BRD expression vector, a europium-labeled anti-Flag antibody (manufactured by Cisbio), and XL-665-labeled avidin (manufactured by Cisbio) were added, and the mixture was reacted at room temperature for 30 min to 2 hr. The fluorescence by FRET was measured by EnVision 2103 Multilabel Reader (manufactured by Perkin Elmer). The binding inhibitory activity was shown by a decrease rate of the count of the compound addition group to that of the compound non-addition group, and $IC_{50}$ value was determined from a dose-reaction curve plotting a decrease rate of the count obtained by changing the compound concentration and the compound concentrations.

The $IC_{50}$ (nmol/L) value of Compound 1 was 55.5 for acetylated histone H4-BRD2, 120.2 for acetylated histone H4-BRD3, and 136.1 for acetylated histone H4-BRD4. The $IC_{50}$ values of other compounds are shown in Table 2.

Example 2

Growth Suppressive Activity Test Against Cancer Cells

Using RPMI 1640 medium (manufactured by SIGMA) supplemented with 10% fetal bovine serum, human promyelocytic leukemia-derived cell line HL-60, human acute lymphoblastic leukemia-derived cell line MOLT4, human Burkitt's lymphoma-derived cell line Daudi, and human multiple myeloma-derived cell line RPMI-8226 were respectively cultured at 37° C., 5% $CO_2$. In addition, using ISKOV medium (manufactured by SIGMA) supplemented with 10% fetal bovine serum, human chronic myeloid leukemia-derived cell line MV4-11 was cultured at 37° C., 5% $CO_2$. Moreover, using DMEM/F-12 medium (manufactured by SIGMA) supplemented with 10% fetal bovine serum, human lung cancer cell-derived cell line EBC-1, human hepatocellular cancer-derived cell line Kim-1, human colorectal cancer-derived cell line HCT-116, human prostate cancer-derived cell line PC-3, human ovarian cancer-derived cell line A2780, and human osteosarcoma-derived cell line Saos2 were respectively cultured at 37° C., 5% $CO_2$. These cells were plated on a 96 well plate, and cultured for 1 day. Thereto was added a compound diluted with the medium to a final concentration of 0.0003-10 μM (final DMSO concentration, 0.4%). After culture for 3 more days, WST-8 (0.16 mg/mL) was added to the culture medium and the cells were cultured for 2 hr. The absorbance at 650 nm was subtracted from the absorbance at 450 nm. The growth suppressive activity was shown by a decrease rate of the absorbance of the compound addition group to that of the compound non-addition group, and $GI_{50}$ value was determined from a dose-reaction curve plotting a decrease rate of the absorbance obtained by changing the compound concentration and the compound concentrations.

The $GI_{50}$ (μmol/L) values of Compounds 1 and 2 are shown in Table 1.

Table 1 Cell Proliferation Suppressive Activity of Compounds 1 and 2 Against Cancer Types

TABLE 1

| cell line derived cancer type | cell line | cell proliferation suppressive activity $GI_{50}$ (μmol/L) | |
|---|---|---|---|
| | | Compound 1 | Compound 2 |
| promyelocytic leukemia | HL-60 | 0.149 | 0.007 |
| chronic myeloid leukemia | MV4-11 | 0.0607 | 0.019 |
| Burkitt's lymphoma | Daudi | 0.611 | 0.0674 |
| multiple myeloma | RPMI-8226 | 0.1299 | 0.06944 |
| hepatocellular cancer | Kim-1 | 0.569 | 0.1036 |
| acute lymphoblastic leukemia | MOLT-4 | 0.08 | 0.106 |
| ovarian cancer | A-2780 | 0.6191 | 0.1295 |
| prostate cancer | PC-3 | 1.03 | 0.199 |
| non-small cell lung cancer | EBC-1 | 0.491 | 0.2071 |
| osteosarcoma | Saos2 | 0.4807 | 0.2686 |
| colorectal cancer | HCT-116 | 0.5633 | 0.356 |

The $GI_{50}$ (nmol/L) values of other compounds are shown in Table 2.

Table 2 Test Results of Compounds 2-18

TABLE 2

| | binding inhibitory activity on acetylated histone H4 and BRD4 $IC_{50}$ (nmol/L) | growth suppressive activity on MV4-11 $GI_{50}$ (nmol/L) |
|---|---|---|
| compound 2 | 121.2 | 19 |
| compound 3 | 54.9 | 20 |
| compound 4 | 77.2 | 95 |
| compound 5 | 54.2 | 73 |
| compound 6 | 18.2 | 26 |
| compound 7 | 113.0 | 55 |
| compound 8 | 123.5 | 9 |
| compound 9 | 73.6 | 39 |
| compound 10 | 47.1 | 7 |
| compound 11 | 225.3 | 95 |
| compound 12 | 107.8 | 30 |
| compound 13 | 17.3 | 22 |
| compound 14 | 21.0 | 42 |
| compound 15 | 119.8 | 34 |
| compound 16 | 116.4 | 28 |
| compound 17 | 12.8 | 14 |
| compound 18 | 146.8 | 48 |

From the above results, it has been clarified that a compound that inhibits binding between acetylated histone, more specifically acetylated histone H4, and a bromodomain-containing protein, more specifically human-derived BET family protein BRD2, BRD3 or BRD4 can be used as an antitumor agent. Moreover, it has also been clarified that a thienotriazolodiazepine compound represented by the above-mentioned formula (I), which inhibits binding between acetylated histone and a bromodomain-containing protein, is useful as an antitumor agent. Furthermore, it has been clarified that a thienotriazolodiazepine compound represented by the above-mentioned formula (I) has a binding inhibitory activity against acetylated histone and a bromodomain-containing protein.

INDUSTRIAL APPLICABILITY

According to the present invention, a novel antitumor agent can be provided.

This application is based on a patent application No. 2007-339456 filed in Japan, the contents of which are incorporated in full herein.

The invention claimed is:

1. A method of shrinking, killing, or inhibiting the growth of cancer cells in a mammal, comprising administering an effective amount of
a thienotriazolodiazepine compound represented by the following formula (I)

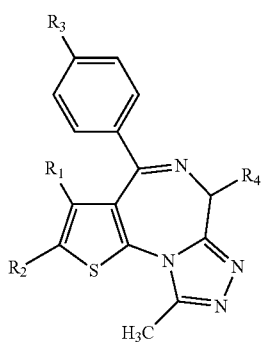

wherein
$R_1$ is alkyl having a carbon number of 1-4,
$R_2$ is a hydrogen atom; a halogen atom; or alkyl having a carbon number of 1-4 optionally substituted by a halogen atom or a hydroxyl group,
$R_3$ is a halogen atom; phenyl optionally substituted by a halogen atom, alkyl having a carbon number of 1-4, alkoxy having a carbon number of 1-4 or cyano; —$NR_5$—$(CH_2)_m$—$R_6$ wherein $R_5$ is a hydrogen atom or alkyl having a carbon number of 1-4, m is an integer of 0-4, and $R_6$ is phenyl or pyridyl optionally substituted by a halogen atom; or —$NR_7$—CO—$(CH_2)_n$—$R_8$ wherein $R_7$ is a hydrogen atom or alkyl having a carbon number of 1-4, n is an integer of 0-2, and $R_8$ is phenyl or pyridyl optionally substituted by a halogen atom, and
$R_4$ is —$(CH_2)_a$—CO—NH—$R_9$ wherein a is an integer of 1-4, and $R_9$ is alkyl having a carbon number of 1-4; hydroxyalkyl having a carbon number of 1-4; alkoxy having a carbon number of 1-4; or phenyl or pyridyl optionally substituted by alkyl having a carbon number of 1-4, alkoxy having a carbon number of 1-4, amino or a hydroxyl group) or —$(CH_2)_b$—$COOR_{10}$ wherein b is an integer of 1-4, and $R_{10}$ is alkyl having a carbon number of 1-4, or a pharmaceutically acceptable salt thereof or (S)-2-[4-(4-chlorophenyl)-2,3,9-trimethyl-6H-thieno[3,2-f][1,2,4]triazolo[4,3-a][1,4]diazepin-6-yl]-N-(4-hydroxyphenyl)acetamide dihydrate
to a mammal with cancer cells, wherein the cancer is hematologic cancer, myeloma, liver cancer, ovarian cancer, prostate cancer, lung cancer, osteosarcoma, or colorectal cancer, whereupon the cancer cells are shrunk or killed in the mammal or the growth of the cancer cells is inhibited in the mammal.

2. The method according to claim 1, wherein the steric configuration of an asymmetric carbon atom to which substituent $R_4$ in the formula (I) is bonded is an S configuration.

3. The method according to claim 1, wherein $R_1$ is methyl.

4. The method according to claim 1, wherein $R_2$ is methyl.

5. The method according to claim 1, wherein $R_3$ is a chlorine atom, cyanophenyl, phenylamino, or phenethylcarbonylamino.

6. The method according to claim 1, wherein $R_4$ is hydroxyphenylaminocarbonylmethyl or methoxycarbonylmethyl.

7. The method according to claim 1, wherein the compound represented by the formula (I) is
(S)-2-[4-(4-chlorophenyl)-2,3,9-trimethyl-6H-thieno[3,2-f][1,2,4]triazolo[4,3-a][1,4]diazepin-6-yl]-N-(4-hydroxyphenyl)acetamide or a dihydrate thereof,
methyl (S)-{4-(3'-cyanobiphenyl-4-yl)-2,3,9-trimethyl-6H-thieno[3,2-f][1,2,4]triazolo[4,3-a][1,4]diazepin-6-yl}acetate,
methyl (S)-{2,3,9-trimethyl-4-(4-phenylaminophenyl)-6H-thieno[3,2-f][1,2,4]triazolo[4,3-a][1,4]diazepin-6-yl}acetate, or
methyl (S)-{2,3,9-trimethyl-4-[4-(3-phenylpropionylamino)phenyl]-6H-thieno[3,2-f][1,2,4]triazolo[4,3-a][1,4]diazepin-6-yl}acetate.

8. The method according to claim 1, wherein the hematologic cancer is lymphoma or leukemia.

9. A method of shrinking or killing of hematologic cancer cells or inhibiting the growth of hematologic cancer cells in a mammal, comprising administering an effective amount of (S)-2-[4-(4-chlorophenyl)-2,3,9-trimethyl-6H-thieno[3,2-f][1,2,4]triazolo[4,3-a][1,4]diazepin-6-yl]-N-(4-hydroxyphenyl)acetamide or a dihydrate thereof to a mammal with hematologic cancer cells, whereupon the hematologic cancer cells are shrunk or killed in the mammal or the growth of the hematologic cancer cells is inhibited in the mammal.

10. A method of shrinking or killing of lymphoma cells or inhibiting the growth of lymphoma cells in a mammal, comprising administering an effective amount of (S)-2-[4-(4-chlorophenyl)-2,3,9-trimethyl-6H-thieno[3,24-f][1,2,4]triazolo[4,3-a][1,4]diazepin-6-yl]-N-(4-hydroxyphenyl)
acetamide or a dihydrate thereof to a mammal with lymphoma cells, whereupon the lymphoma cells are shrunk or killed in the mammal or the growth of the lymphoma cells is inhibited in the mammal.

11. A method of shrinking or killing of leukemia cells or inhibiting the growth of leukemia cells in a mammal, comprising administering an effective amount of (S)-2-[4-(4-chlorophenyl)-2,3,9-trimethyl-6H-thieno[3,2-f][1,2,4]triazolo[4,3-a][1,4]diazepin-6-yl]-N-(4-hydroxyphenyl)
acetamide or a dihydrate thereof to a mammal with leukemia cells, whereupon the leukemia cells are shrunk or killed in the mammal or the growth of the leukemia cells is inhibited in the mammal.

12. A method of shrinking or killing of myeloma cells or inhibiting the growth of myeloma cells in a mammal, comprising administering an effective amount of (S)-2-[4-(4-chlorophenyl)-2,3,9-trimethyl-6H-thieno[3,2-f][1,2,4]triazolo[4,3-a][1,4]diazepin-6-yl]-N-(4-hydroxyphenyl) acetamide or a dihydrate thereof to a mammal with myeloma cells, whereupon the myeloma cells are shrunk or killed in the mammal or the growth of the myeloma cells is inhibited in the mammal.

13. A method of shrinking or killing of lung cancer cells or inhibiting the growth of lung cancer cells in a mammal, comprising administering an effective amount of (S)-2-[4-(4-chlorophenyl)-2,3,9-trimethyl-6H-thieno[3,2-f][1,2,4]triazolo[4,3-a][1,4]diazepin-6-yl]-N-(4-hydroxyphenyl) acetamide or a dihydrate thereof to a mammal with lung cancer cells, whereupon the lung cancer cells are shrunk or killed in the mammal or the growth of the lung cancer cells is inhibited in the mammal.

* * * * *

UNITED STATES PATENT AND TRADEMARK OFFICE
CERTIFICATE OF CORRECTION

PATENT NO.       : 8,476,260 B2                                Page 1 of 1
APPLICATION NO.  : 12/810564
DATED            : July 2, 2013
INVENTOR(S)      : Miyoshi et al.

It is certified that error appears in the above-identified patent and that said Letters Patent is hereby corrected as shown below:

IN THE CLAIMS

Claim 10 at column 20, line 49, [3,24-f] should read [3,2-f]

Signed and Sealed this
Twenty-fifth Day of February, 2014

Michelle K. Lee
*Deputy Director of the United States Patent and Trademark Office*